(12) United States Patent
Caboche et al.

(10) Patent No.: US 8,513,195 B2
(45) Date of Patent: Aug. 20, 2013

(54) TREATMENT OF MOOD AND ANXIETY DISORDERS

(75) Inventors: Jocelyne Caboche, Vicq (FR); Eleni Tzavara, Paris (FR); Peter Vanhoutte, Alfortville (FR); Bruno Giros, Chatillon (FR)

(73) Assignees: Universite Pierre et Marie Curie, Paris (FR); Centre National de la Recherche Scientifique-CNRS, Paris Cedex (FR)

( * ) Notice: Subject to any disclaimer, the term of this patent is extended or adjusted under 35 U.S.C. 154(b) by 0 days.

(21) Appl. No.: 13/121,804

(22) PCT Filed: Oct. 2, 2009

(86) PCT No.: PCT/EP2009/062812
§ 371 (c)(1),
(2), (4) Date: Mar. 30, 2011

(87) PCT Pub. No.: WO2010/037841
PCT Pub. Date: Apr. 8, 2010

(65) Prior Publication Data
US 2011/0183909 A1 Jul. 28, 2011

(30) Foreign Application Priority Data

Oct. 3, 2008 (EP) .................................. 08305636

(51) Int. Cl.
*A01N 37/18* (2006.01)
*A61K 38/00* (2006.01)

(52) U.S. Cl.
USPC ........................................ 514/17.6; 514/17.5

(58) Field of Classification Search
None
See application file for complete search history.

(56) References Cited

FOREIGN PATENT DOCUMENTS

| | | |
|---|---|---|
| EP | 1693458 | 8/2006 |
| WO | 2005/097758 | 10/2005 |
| WO | 2006/087242 | 8/2006 |

OTHER PUBLICATIONS

Buchanan et al., J. Nat. Prod., 64(3):300-303 (2001) XP002516143.
Einat et al., J. Neurosci., 23(19):7311-7316 (2003) XP002496986.
International Search Report and Written Opinion in PCT/EP2009/062812, dated Jan. 7, 2010.
Joo Joung Hyuck et al., J. Biol. Chem., 283(24):16391-16399 (2008) XP002516144.
Hancock et al., J. Med. Chem., 48:4586-4595 (2005).

*Primary Examiner* — Olga N Chernyshev
(74) *Attorney, Agent, or Firm* — McAndrews, Held & Malloy Ltd.

(57) ABSTRACT

The invention relates to a selective inhibitor of Elk-1 or MSK-1 activation for use in the prevention and/or treatment of mood and anxiety disorders.

4 Claims, 9 Drawing Sheets

SEQUENCE LISTING

```
<160> NUMBER OF SEQ ID NOS: 30

<210> SEQ ID NO 1
<211> LENGTH: 19
<212> TYPE: PRT
<213> ORGANISM: artificial
<220> FEATURE:
<223> OTHER INFORMATION: Elk-1 docking domain

<400> SEQUENCE: 1

Ser Pro Ala Lys Leu Ser Phe Gln Phe Pro Ser Ser Gly Ser Ala Gln
1               5                   10                  15

Val His Ile

<210> SEQ ID NO 2
<211> LENGTH: 17
<212> TYPE: PRT
<213> ORGANISM: artificial
<220> FEATURE:
<223> OTHER INFORMATION: Elk-1 docking domain

<400> SEQUENCE: 2

Lys Gly Arg Lys Pro Arg Asp Leu Glu Leu Pro Leu Ser Pro Ser Leu
1               5                   10                  15

Leu

<210> SEQ ID NO 3
<211> LENGTH: 18
<212> TYPE: PRT
<213> ORGANISM: artificial
<220> FEATURE:
<223> OTHER INFORMATION: MSK-1 docking domain

<400> SEQUENCE: 3

Lys Ala Pro Leu Ala Lys Arg Arg Lys Met Lys Lys Thr Ser Thr Ser
1               5                   10                  15

Thr Glu

<210> SEQ ID NO 4
<211> LENGTH: 10
<212> TYPE: PRT
<213> ORGANISM: artificial
<220> FEATURE:
<223> OTHER INFORMATION: HIV-TAT cell penetrating sequence

<400> SEQUENCE: 4

Gly Arg Lys Lys Arg Arg Gln Arg Arg Arg
1               5                   10

<210> SEQ ID NO 5
<211> LENGTH: 16
<212> TYPE: PRT
<213> ORGANISM: artificial
```

```
<220> FEATURE:
<223> OTHER INFORMATION: Penetratine cell penetrating sequence

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 7
<212> TYPE: PRT
<213> ORGANISM: artificial
<220> FEATURE:
<223> OTHER INFORMATION: 7R cell penetrating sequence

<400> SEQUENCE: 6

Arg Arg Arg Arg Arg Arg Arg
1               5

<210> SEQ ID NO 7
<211> LENGTH: 8
<212> TYPE: PRT
<213> ORGANISM: artificial
<220> FEATURE:
<223> OTHER INFORMATION: 8R cell penetrating sequence

<400> SEQUENCE: 7

Arg Arg Arg Arg Arg Arg Arg Arg
1               5

<210> SEQ ID NO 8
<211> LENGTH: 9
<212> TYPE: PRT
<213> ORGANISM: artificial
<220> FEATURE:
<223> OTHER INFORMATION: 9R cell penetrating sequence

<400> SEQUENCE: 8

Arg Arg Arg Arg Arg Arg Arg Arg Arg
1               5

<210> SEQ ID NO 9
<211> LENGTH: 10
<212> TYPE: PRT
<213> ORGANISM: artificial
<220> FEATURE:
<223> OTHER INFORMATION: 10R cell penetrating sequence

<400> SEQUENCE: 9

Arg Arg Arg Arg Arg Arg Arg Arg Arg Arg
1               5                   10

<210> SEQ ID NO 10
<211> LENGTH: 11
<212> TYPE: PRT
<213> ORGANISM: artificial
<220> FEATURE:
<223> OTHER INFORMATION: 11R cell penetrating sequence

<400> SEQUENCE: 10

Arg Arg Arg Arg Arg Arg Arg Arg Arg Arg
1               5                   10

<210> SEQ ID NO 11
<211> LENGTH: 8
<212> TYPE: PRT
<213> ORGANISM: artificial
<220> FEATURE:
<223> OTHER INFORMATION: XR cell penetrating sequence
```

```
<220> FEATURE:
<221> NAME/KEY: misc_feature
<222> LOCATION: (1)..(1)
<223> OTHER INFORMATION: Xaa can be any naturally occurring amino acid

<400> SEQUENCE: 11

Xaa Arg Arg Arg Arg Arg Arg
1               5

<210> SEQ ID NO 12
<211> LENGTH: 8
<212> TYPE: PRT
<213> ORGANISM: artificial
<220> FEATURE:
<223> OTHER INFORMATION: RX cell penetrating sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 12

Arg Arg Arg Arg Arg Arg Arg Xaa
1               5

<210> SEQ ID NO 13
<211> LENGTH: 9
<212> TYPE: PRT
<213> ORGANISM: artificial
<220> FEATURE:
<223> OTHER INFORMATION: XRX cell penetrating sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 13

Xaa Arg Arg Arg Arg Arg Arg Arg Xaa
1               5

<210> SEQ ID NO 14
<211> LENGTH: 14
<212> TYPE: PRT
<213> ORGANISM: artificial
<220> FEATURE:
<223> OTHER INFORMATION: XRX cell penetrating sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 14

Xaa Arg Arg Arg Arg Arg Arg Xaa Arg Arg Arg Arg Arg Xaa
1               5                   10

<210> SEQ ID NO 15
<211> LENGTH: 23
<212> TYPE: PRT
<213> ORGANISM: artificial
<220> FEATURE:
<223> OTHER INFORMATION: DPV15b cell penetrating sequence
```

```
<400> SEQUENCE: 15

Gly Ala Tyr Asp Leu Asp Arg Arg Glu Arg Gln Ser Arg Leu Arg
1               5                   10                  15

Arg Arg Glu Arg Gln Ser Arg
            20

<210> SEQ ID NO 16
<211> LENGTH: 14
<212> TYPE: PRT
<213> ORGANISM: artificial
<220> FEATURE:
<223> OTHER INFORMATION: DPV10 cell penetrating sequence

<400> SEQUENCE: 16

Ser Arg Arg Ala Arg Ser Pro Arg His Leu Gly Ser Gly
1               5                   10

<210> SEQ ID NO 17
<211> LENGTH: 16
<212> TYPE: PRT
<213> ORGANISM: artificial
<220> FEATURE:
<223> OTHER INFORMATION: DPV15 cell penetrating sequence

<400> SEQUENCE: 17

Leu Arg Arg Glu Arg Gln Ser Arg Leu Arg Arg Glu Arg Gln Ser Arg
1               5                   10                  15

<210> SEQ ID NO 18
<211> LENGTH: 19
<212> TYPE: PRT
<213> ORGANISM: artificial
<220> FEATURE:
<223> OTHER INFORMATION: DPV1047 cell penetrating sequence

<400> SEQUENCE: 18

Val Lys Arg Gly Leu Lys Leu Arg His Val Arg Pro Arg Val Thr Arg
1               5                   10                  15

Met Asp Val

<210> SEQ ID NO 19
<211> LENGTH: 16
<212> TYPE: PRT
<213> ORGANISM: artificial
<220> FEATURE:
<223> OTHER INFORMATION: DPV3 cell penetrating sequence

<400> SEQUENCE: 19

Arg Lys Lys Arg Arg Arg Glu Ser Arg Lys Lys Arg Arg Arg Glu Ser
1               5                   10                  15

<210> SEQ ID NO 20
<211> LENGTH: 7
<212> TYPE: PRT
<213> ORGANISM: artificial
<220> FEATURE:
<223> OTHER INFORMATION: SV40 large T antigen NLS sequence

<400> SEQUENCE: 20

Pro Lys Lys Lys Arg Lys Val
1               5

<210> SEQ ID NO 21
<211> LENGTH: 16
<212> TYPE: PRT
<213> ORGANISM: artificial
```

```
<220> FEATURE:
<223> OTHER INFORMATION: nucleoplasmin NLS sequence

<400> SEQUENCE: 21

Lys Arg Pro Ala Ala Ile Lys Lys Ala Gly Gln Ala Lys Lys Lys
1               5                   10                  15

<210> SEQ ID NO 22
<211> LENGTH: 15
<212> TYPE: PRT
<213> ORGANISM: artificial
<220> FEATURE:
<223> OTHER INFORMATION: HIV1rev NLS sequence

<400> SEQUENCE: 22

Arg Gln Ala Arg Arg Asn Arg Arg Asn Arg Arg Arg Trp Arg
1               5                   10                  15

<210> SEQ ID NO 23
<211> LENGTH: 12
<212> TYPE: PRT
<213> ORGANISM: artificial
<220> FEATURE:
<223> OTHER INFORMATION: Elk-1 type consensus NES sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Xaa Leu Xaa Xaa Xaa Leu Xaa Xaa Leu Xaa Leu Xaa
1               5                   10

<210> SEQ ID NO 24
<211> LENGTH: 12
<212> TYPE: PRT
<213> ORGANISM: artificial
<220> FEATURE:
<223> OTHER INFORMATION: Net  type consensus NES sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
```

```
<220> FEATURE:
<221> NAME/KEY: misc_feature
<222> LOCATION: (12)..(12)
<223> OTHER INFORMATION: Xaa can be any naturally occurring amino acid

<400> SEQUENCE: 24

Xaa Leu Xaa Xaa Xaa Leu Xaa Xaa Leu Xaa Arg Xaa
1               5                   10

<210> SEQ ID NO 25
<211> LENGTH: 12
<212> TYPE: PRT
<213> ORGANISM: artificial
<220> FEATURE:
<223> OTHER INFORMATION: MAPKK NES sequence

<400> SEQUENCE: 25

Ala Leu Gln Lys Lys Leu Glu Glu Leu Glu Leu Asp
1               5                   10

<210> SEQ ID NO 26
<211> LENGTH: 12
<212> TYPE: PRT
<213> ORGANISM: artificial
<220> FEATURE:
<223> OTHER INFORMATION: Net NES sequence

<400> SEQUENCE: 26

Thr Leu Trp Gln Phe Leu Leu Gln Leu Leu Leu Asp
1               5                   10

<210> SEQ ID NO 27
<211> LENGTH: 12
<212> TYPE: PRT
<213> ORGANISM: artificial
<220> FEATURE:
<223> OTHER INFORMATION: Elk-1  NES sequence

<400> SEQUENCE: 27

Thr Leu Trp Gln Phe Leu Leu Gln Leu Leu Arg Glu
1               5                   10

<210> SEQ ID NO 28
<211> LENGTH: 31
<212> TYPE: PRT
<213> ORGANISM: artificial
<220> FEATURE:
<223> OTHER INFORMATION: selective peptide inhibitor of Elk-1
      activation - TAT-DEF-Elk-1

<400> SEQUENCE: 28

Gly Arg Lys Lys Arg Arg Gln Arg Arg Arg Pro Pro Ser Pro Ala Lys
1               5                   10                  15

Leu Ser Phe Gln Phe Pro Ser Ser Gly Ser Ala Gln Val His Ile
            20                  25                  30

<210> SEQ ID NO 29
<211> LENGTH: 29
<212> TYPE: PRT
<213> ORGANISM: artificial
<220> FEATURE:
<223> OTHER INFORMATION: selective peptide inhibitor of ELk-1 activation
```

```
-continued

<400> SEQUENCE: 29

Gly Arg Lys Lys Arg Arg Gln Arg Arg Arg Pro Pro Lys Gly Arg Lys
1               5                   10                  15

Pro Arg Asp Leu Glu Leu Pro Leu Ser Pro Ser Leu Leu
            20                  25

<210> SEQ ID NO 30
<211> LENGTH: 30
<212> TYPE: PRT
<213> ORGANISM: artificial
<220> FEATURE:
<223> OTHER INFORMATION: selective inhibitor of MSK-1 activation

<400> SEQUENCE: 30

Gly Arg Lys Lys Arg Arg Gln Arg Arg Arg Pro Pro Lys Ala Pro Leu
1               5                   10                  15

Ala Lys Arg Arg Lys Met Lys Lys Thr Ser Thr Ser Thr Glu
            20                  25                  30
```

TREATMENT OF MOOD AND ANXIETY DISORDERS

The present application is filed pursuant to 35 U.S.C. 371 as a U.S. National Phase application of International Patent Application No. PCT/EP09/62812, which was filed Oct. 2, 2009, claiming the benefit of priority to European Patent Application No. 08305636.6, which was filed on Oct. 3, 2008. The entire text of the aforementioned applications is incorporated herein by reference in its entirety.

FIELD OF THE INVENTION

The invention relates to the use of selective inhibitors of Elk-1 and MSK-1 activation for treating mood and anxiety disorders.

BACKGROUND OF THE INVENTION

Depression is a common, life-disrupting, potentially lethal illness that can affect both sexes and all ages, and that is characterized by sadness, loss of interest or pleasure, feelings of guilt or low self-worth, disturbed sleep or appetite, low energy and poor concentration. These problems can become chronic or recurrent, substantially impairing an individual's ability to cope with daily life. At its most severe, depression can lead to suicide. Untreated major depression thus remains a serious public health problem ands its incidences are staggering.

The economic costs to society, and person costs to individuals and families, associated with depression are enormous. Within a 15-month period after having been diagnosed with depression, sufferers are four times more likely to die as those who do not have depression. The World Health Organization estimates that major depression is the fourth most important cause worldwide of loss in disability-adjusted life years, and will be the second most important cause by 2020.

Depression has no single cause; often, it results from a combination of factors. Whatever its cause, depression is not just a state of mind. It is related to long lasting changes in the brain, and connected to an imbalance of a type of chemical that carries signals in the brain and nerves. These chemicals are called neurotransmitters. Among the most important neurotransmitters related to depression are serotonin (5-HT), norepinephrine (NE), and dopamine (DA). Serotonin plays a very important role in mood disorders, especially in anxiety and depression, aggression and impulsivity.

Most cases of depression can be treated with medication or psychotherapy. A variety of pharmacological agents are available for the treatment of depression. Significant success has been achieved through the use of serotonin-selective reuptake inhibitors (SSRIs), such as fluoxetine (PROZAC®), norepinephrine reuptake inhibitors (NERIs), combined serotonin-norepinephrine reuptake inhibitors (SNRIs), monoamine oxidase inhibitors (MAOIs), phosphodiesterase-4 (PDE4) inhibitors or other compounds. However, even with these options available, many patients fail to respond, or respond only partially to the treatment. Additionally, many of these agents show delayed onset of activity, so that patients are required to undergo treatment for weeks or months before receiving benefits. Most currently available antidepressants take 2-3 weeks or more to elicit a response.

Traditional therapies can also have significant side effects. For example, more than a third of patients taking SSRIs experience sexual dysfunction. Other problematic side effects include gastrointestinal disturbances, often manifested as nausea and occasional vomiting, agitation, insomnia, weight gain, onset of diabetes, prolongation of the heart rate corrected interval (QTc), agranulocytosis, etc. The side effects often discourage patients from following their recommended therapeutic regimen.

Therefore, there remains a need for the development of improved therapies for the treatment of depression and/or other mood and anxiety disorders.

SUMMARY OF THE INVENTION

One object of the invention is a selective inhibitor of Elk-1 or MSK-1 activation for use in the prevention and/or treatment of mood and anxiety disorders.

In one embodiment, said selective inhibitor of Elk-1 activation is a peptide comprising:
 at least one cell penetrating sequence, and
 at least one docking domain sequence selected in the group of SEQ ID NO: 1 (SPAKLSFQFPSSGSAQVHI) and SEQ ID NO: 2 (KGRKPRDLELPLSPSLL).

In another embodiment, said selective inhibitor of MSK-1 activation is a peptide comprising:
 at least one cell penetrating sequence, and
 a docking domain sequence selected in the group of SEQ ID NO: 3 (KAPLAKRRKMKKTSTSTE).

In another embodiment, said cell penetrating sequence is chosen in the group comprising HIV-TAT sequence (SEQ ID NO: 4); Penetratin (SEQ ID NO: 5); an amino acid sequence of 7 to 11 arginine (SEQ ID NO: 6 to 10); a X7/11R sequence of 7 to 25 amino acids comprising 7 to 11 arginine randomly positioned in the sequence; or a sequence derived from DPVs (SEQ ID NO: 15 to 19).

In another embodiment, said selective inhibitor of Elk-1 activation has the sequence SEQ ID NO: 28 or SEQ ID NO: 29.

In another embodiment, said selective inhibitor of MSK-1 activation has the sequence SEQ ID NO: 30.

Another object of the invention is a pharmaceutical composition for use in preventing and/or treating mood and anxiety disorders, wherein said pharmaceutical composition comprises at least one selective inhibitor of Elk-1 or MSK-1 activation.

In one embodiment, said pharmaceutical composition comprises:
a) at least one selective inhibitor of Elk-1 or MSK-1 activation;
b) a nucleic acid encoding a peptide inhibitor of Elk-1 or MSK-1 activation; or
c) an expression vector comprising said nucleic acid.

Another object of the invention is a selective inhibitor of Elk-1 or MSK-1 activation or a pharmaceutical composition as described here above, for use in treating depression.

Another object of the invention is a method for treating mood and anxiety disorders in a subject in need thereof, said method comprising administering a therapeutically effective amount of at least one selective peptide inhibitor of Elk-1 or MSK-1 activation or a therapeutically amount of a pharmaceutical composition as described here above.

DETAILED DESCRIPTION OF THE INVENTION

Definitions

As used herein, the term "peptide" refers to an amino acid sequence having less than 100 amino acids. As used herein, the term "peptide" encompasses amino acid sequences having less than 90 amino acids, less than 80 amino acids, less than 70 amino acids, less than 60 amino acids, or less than 50 amino acids. Preferably, said amino acid sequence comprises 20, 21, 22, 23, 24, 25, . . . , 50, . . . , . . . , 75, . . . , 100 amino acids.

"Function-conservative variants" as used herein refer to those peptides in which a given amino acid residue in a protein or enzyme has been changed (inserted, deleted or substituted) without altering the overall conformation and function of the polypeptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

As used herein, the term "treating" a disorder or a condition refers to reversing, alleviating or inhibiting the process of one or more symptoms of such disorder or condition. The term "preventing" a disorder or condition refers to preventing one or more symptoms of such disorder or condition.

As used herein, "mood disorder" refers to disruption of feeling tone or emotional state experienced by an individual for an extensive period of time. Mood disorders include, but are not limited to, major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

As used herein, anxiety disorders refers to unpleasant emotional state comprising psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. Anxiety disorders include, but are not limited to, panic disorder, obsessive-compulsive disorder, post-traumatic stress disorder, social phobia, social anxiety disorder, specific phobias, generalized anxiety disorder "Obsessive compulsive disorder" or "OCD" is an anxiety disorder characterized by recurrent obsessions or compulsions sufficient to cause marked distress in the individual. They are typically time-consuming, and/or significantly interfere with the person's normal functioning, social activities, or relationships. Obsessions are recurrent ideas, thoughts, images, or impulses that enter the mind and are persistent, intrusive, and unwelcome. Often, attempts are made to ignore or suppress the thoughts, or to neutralize them with some other thought or action. The individual may recognize the obsessions as a product of his or her own mind. Compulsions are repetitive, purposeful behaviors or movements performed in response to an obsession, and are typically designed to neutralize or prevent discomfort or some dreaded event or situation. For example, a common obsession concerns thoughts of contamination; excessive, repetitive, and non-purposeful handwashing is a common compulsion.

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability, or persistent physical symptoms that do not respond to treatment, such as headaches digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing try being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV. As used herein, the term "subject" denotes a mammal, such as a rodent, a feline, a canine, and a primate. Preferably a subject according to the invention is a human.

A "therapeutically effective amount" as used herein is intended for a minimal amount of active agent which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

The Invention

Recently, as the MERK-ERK signalling pathway is susceptible to environmental and genetic regulations relevant to depression, it was investigated for providing targets for the development of novel therapy. However, studies with the MEK inhibitor SL327 in depression have been inconclusive, with sometimes opposing results (Duman et al., Biol Psychiatry 2007; Einat et al, J Neurosci, 2003). In contrast to Einat et al. that demonstrate antidepressant-like action after inhibition of ERK activation, Duman's study, using inhibitors of ERK activation, demonstrated that acute blockade of MERK-ERK signalling produces a depressive-like phenotype in three models of depression. The authors thus suggested that drugs that activate the MERK-ERK pathway should produce an antidepressant response.

While searching for novel pharmacotherapeutics for treating depression, the inventors postulated that a MEK inhibitor (like SL327 and PD184161) used above, was an unselective tool that does not permit differentiation among the multiple downstream substrates of ERK and thus investigated whether or not a blockade of ERK-mediated gene regulation could lead to an antidepressant response.

ERK-mediated gene regulation is mainly controlled by two factors: Elk-1 and MSK-1. Elk-1 is a transcription factor present in the nucleus, which regulates gene expression via promoters with serum-responsive elements (SRE). MSK-1 also regulates gene expression via the phosphorylation of c-AMP-responsive element binding protein (CREB) and histone H3 and hence chromatin remodelling.

The inventors then surprisingly found that a selective inhibitor of Elk-1 activation, which is implied in ERK-mediated gene regulation, acts as an antidepressant agent and thus has an effect on mood and anxiety disorders.

One object of the invention is a selective inhibitor of Elk-1 or MSK-1 activation for the prevention and/or treatment of anxiety and mood disorders.

Another object of the invention is a selective inhibitor of Elk-1 or Msk-1 activation for use in the prevention and/or the treatment of anxiety and mood disorders.

According to the invention, said "selective inhibitor of Elk-1 or MSK-1 activation" refers to an inhibitor that inhibits specifically the activation of Elk-1 or MSK-1 respectively without modifying the activation of ERK or other targets of ERK including p90RSK, synapsin, PLP2A, Tyrosine Hydroxylase.

In one embodiment of the invention, said selective inhibitor of Elk-1 activation is the compound 76 described in Hancock et al., Journal of Medicinal Chemistry, 2005, 48(14): 4586-4595.

In one embodiment of the invention, said selective inhibitor of Elk-1 activation for the prevention and/or treatment of anxiety and mood disorders, wherein said inhibitor of Elk-1 activation is a peptide comprising:
  at least one cell penetrating sequence, and
  at least one docking domain sequence selected in the group of SEQ ID NO: 1 (SPAKLSFQFPSSGSAQVHI) and SEQ ID NO: 2 (KGRKPRDLELPLSPSLL).

In one embodiment of the invention, said selective inhibitor of MSK-1 activation for the prevention and/or treatment of anxiety and mood disorders, wherein said inhibitor of MSK-1 activation is a peptide comprising:
  at least one cell penetrating sequence, and
  a docking domain sequence selected in the group of SEQ ID NO: 3 (KAPLAKRRKMKKTSTSTE).

Said peptide inhibitors of Elk-1 or MSK-1 activation were described in WO2006/087242.

In one embodiment of the invention, said cell penetrating sequence is chosen in the group comprising HIV-TAT sequence (SEQ ID NO: 4); Penetratin (SEQ ID NO: 5); an amino acid sequence of 7 to 11 arginine (SEQ ID NO: 6 to 10); a X7/11R sequence wherein said sequence is a 7 to 25 amino acid sequence, preferably a 7 to 20 amino acid sequence, comprising 7 to 11 arginine randomly positioned in the sequence; or a sequence derived from the Vectocell® (or Diatos peptide vectors: DPVs) as cell penetrating sequences described in De Coupade et al. Biochem J (2005) 390, 407-418 et WO01/64738.

Examples of X7/11R sequences and DPV sequences are given in the following table.

| SEQ ID NO: 4 | GRKKRRQRRR | HIV-TAT |
|---|---|---|
| SEQ ID NO: 5 | RQIKIWFQNRRMKWKK | Penetratine |
| SEQ ID NO: 6 | RRRRRRR | 7R |
| SEQ ID NO: 7 | RRRRRRRR | 8R |
| SEQ ID NO: 8 | RRRRRRRRR | 9R |
| SEQ ID NO: 9 | RRRRRRRRRR | 10R |
| SEQ ID NO: 10 | RRRRRRRRRRR | 11R |
| SEQ ID NO: 11 | XRRRRRRR | X7R (example) |
| SEQ ID NO: 12 | RRRRRRRX | X7R (other example) |
| SEQ ID NO: 13 | XRRRRRRRX | X7R (other example) |
| SEQ ID NO: 14 | XRRRRRRXRRRRRX | X11R (other example) |
| SEQ ID NO: 15 | GAYDLDRRRERQSRLRRRE RQSR | DPV15b |
| SEQ ID NO: 16 | SRRARRSPRHLGSG | DPV10 |
| SEQ ID NO: 17 | LRRERQSRLRRERQSR | DPV15 |
| SEQ ID NO: 18 | VKRGLKLRHVRPRVTRMDV | DPV1047 |
| SEQ ID NO: 19 | RKKRRRESRKKRRRES | DPV3 |

In one embodiment of the invention, the cell penetrating sequence and the docking domain of the peptide inhibitors of the invention can be linked by chemical coupling in any suitable manner known in the art.

One way to increase coupling specificity is to directly chemically couple functional groups found only once or a few times in one or both of the polypeptides to be crosslinked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide has the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. Intermolecular cross-linking reagents which can be utilized are known in the art. Among these reagents are, for example, J-succinimidyl 3-(2-pyridyldithio)propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m' dinitrodiphenylsulfone (which forms irreversible cross-linkages with amino and phenolic groups); dimethyl adipimidate (which is specific for amino groups); phenol-1,4disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiolreactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. For example, said spacer comprises one or more proline, preferably 2, 3 or 4 proline.

Alternatively, a spacer arm may be part of the cross-linking reagent, such as in "long-chain SPDP".

In another embodiment of the invention, said selective peptide inhibitor of Elk-1 or MSK-1 activation further comprise a nuclear localization signal (NLS) sequence and/or a nuclear export sequence (NES) sequence.

Said NLS and NES sequences are well known in the art and comprise 2 to 20 amino acids, preferably 3, 4, 5, ..., 18, 19 or 20 amino acids.

In one embodiment, said NLS and NES sequences are chosen in the following table.

|  |  | origin |
|---|---|---|
| NLS sequence | | |
| SEQ ID NO: 20 | PKKKRKV | SV40 large T-antigen |
| SEQ ID NO: 21 | KRPAAIKKAGQAKKKK | Nucleoplasmin |
| SEQ ID NO: 22 | RQARRNRRNRRRRWR | HIV1Rev |
| SEQ ID NO: 4 | GRKKRRQRRR | HIV-TAT |
| SEQ ID NO: 5 | RQIKIWFQNRRMKWKK | Penetratin |
| SEQ ID NO: 6 | RRRRRRR | 7R |
| SEQ ID NO: 7 | RRRRRRRR | 8R |
| SEQ ID NO: 8 | RRRRRRRRR | 9R |
| SEQ ID NO: 9 | RRRRRRRRRR | 10R |
| SEQ ID NO: 10 | RRRRRRRRRRR | 11R |
| NES sequence | | |
| SEQ ID NO: 23 | XLXXXLXXLXLX | Elk-1 type consensus |
| SEQ ID NO: 24 | XLXXXLXXLXRX | Net type consensus |
| SEQ ID NO: 25 | ALQKKLEELELD | MAPKK |
| SEQ ID NO: 26 | TLWQFLLQLLLD | Net |
| SEQ ID NO: 27 | TLWQFLLQLLRE | Elk-1 |

In another embodiment, peptide inhibitor of Elk-1 or MSK-1 activation further comprise an enzymatic cleavage site, allowing to the cleavage in a cell between the cell penetrating sequence and the rest of the sequence of the peptide inhibitor.

In one embodiment, said enzymatic cleavage site comprises two consecutive cystein residues, allowing the intracellular cleavage by cytoplasmic glutathione.

In one embodiment of the invention, said selective peptide inhibitor of Elk-1 activation has for sequence SEQ ID NO: 28 (GRKKRRQRRRPPSPAKLSFQFPSSGSAQVHI).

In one embodiment of the invention, said selective peptide inhibitor of Elk-1 activation has for sequence SEQ ID NO: 29 (GRKKRRQRRRPPKGRKPRDLELPLSPSLL).

In one embodiment of the invention, said peptide inhibitor of MSK-1 activation has for sequence SEQ ID NO: 30 (GRKKRRQRRRPPKAPLAKRRKMKKTSTSTE).

Typically, the invention encompasses peptides substantially identical to the peptide inhibitors of the invention in which one or more residues have been conservatively substituted with a functionally similar residue and which displays the functional aspects of the peptide inhibitors of the invention as described here above, i.e. being still able to inhibit Elk-1 or MSK-1 activation in substantially the same way as the peptide inhibitors as described here above.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a subject peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In one embodiment of the invention, the peptide inhibitor of Elk-1 or MSK-1 activation consists essentially of an amino acid sequence according to SEQ ID NO: 28 to 30 or a variant thereof.

According to the invention, "consisting essentially of" shall mean that a peptide according to the present invention, in addition to the sequence according to any of SEQ ID No. 28 to 30 or a variant thereof, contains additional N- and/or C-terminally located stretches of amino acids that are not necessarily forming part of the peptide that functions as core sequence of the peptide comprising the binding motif and as an immunogenic epitope.

In one embodiment, the invention also encompasses a salt of peptide of the invention. The term "salt" includes acid addition salts which are formed with inorganic acids such as, for example, hydrochloric or phosphoric acids, or such organic acids as acetic, oxalic, tartaric, mandelic, and the like. The term also includes base addition salts which are formed from inorganic bases such as, for example, sodium, potassium, ammonium, and calcium, and from organic bases such as isopropylamine, trimethylamine, histidine, and the like.

In one embodiment of the invention, the amino acids that make up the peptide inhibitors are L enantiomers. In another embodiment of the invention, one or more amino acids of the peptide sequence can be replaced with its D enantiomer. In another embodiment of the invention, the peptide inhibitor is a all D retro-inverso version of the peptide sequence.

The peptide inhibitors of the invention can be polymers of L-amino acids, D-amino acids, or a combination of both. For example, the peptides are D retro-inverso peptides. The term "retro-inverso isomer" refers to an isomer of a linear peptide in which the direction of the sequence is reversed and the chirality of each amino acid residue is inverted. The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Said peptide inhibitor of Elk-1 or MSK-1 activation may be obtained by conventional techniques known in the art. For example, said peptide inhibitors may be obtained by chemical synthesis, such as conventional solid phase synthesis or liquid phase synthesis. Solid phase synthesis using Boc (t-butyloxycarbonyl) or Fmoc (9-fluorenylmethoxycarbonyl) as the amino protecting group is suitable.

Said peptide inhibitors may also be biosynthesized by genetic engineering methods. This approach is suitable when producing polypeptides with relatively long peptide chains. That is, DNA is synthesized with a nucleotide sequence (including ATG initiation codon) coding for the amino acid sequence of the desired inhibitor peptide. A recombinant vector having a gene expression construct consisting of this DNA together with the various regulatory elements (including promoters, ribosome binding sites, terminators, enhancers, and various cis-elements for controlling expression level) required for expressing the amino acid sequence in host cells is then constructed according to the host cells. A common technique is to introduce this recombinant vector into specific host cells (such as yeast cells, insect cells, plant cells, bacterial cells or animal (mammal) cells), and then culture these host cells, or a tissue or organism containing these cells, under specific conditions. In this way, the target polypeptide can be expressed and produced in the cells. The polypeptide is then isolated and purified from the host cells (or from medium if it is excreted) to thereby obtain the desired inhibitor peptide. Methods conventionally used in the art can be adopted for constructing the recombinant vector and introducing the constructed vector into host cells. For example, a fused protein expression system can be used in order to achieve efficient, high-volume production in host cells. That is, a gene (DNA) coding for the amino acid sequence of the inhibitor peptide is chemically synthesized, and this synthetic DNA is introduced into a suitable site in a suitable fused protein expression vector (for example, a GST (Glutathione S-transferase) fused protein expression vector such as a Novagen pET series or Amersham Biosciences pGEX series vector). Host cells (typically E. coli) are then transformed with this vector. The resulting transformant is cultured to prepare the target fused protein. The protein is extracted and purified. The resulting purified fused protein is cleaved with a specific enzyme (protease), and the released target peptide fragment is collected by a method such as affinity chromatography. The inhibitor peptide of the invention can be produced using such a conventional fused protein expression system (using for example a GST/H is system from Amersham Biosciences). Alternatively, template DNA (that is, a synthetic DNA fragment comprising a nucleotide sequence coding for the amino acid sequence of the inhibitor peptide) for a cell-free protein synthesis system can be constructed, and the target polypeptide can be synthesized in vitro by means of a cell-free protein synthesis system using various compounds (ATP, RNA polymerase, amino acids, etc.) necessary for peptide synthesis.

Nucleic acid sequences encoding the peptide inhibitors of Elk-1 or MSK-1 activation as described here above may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Expression vectors are also provided for recombinant expression of one or more peptide inhibitor of Elk-1 or Msk-1 activation as defined above. The term "expression vector" is used herein to designate either circular or linear DNA or RNA, which is either double-stranded or single-stranded. It further comprises at least one nucleic acid as described here above to be transferred into a host cell or into a unicellular or multicellular host organism. The expression vector preferably comprises a nucleic acid encoding one or more peptide inhibitor of Elk-1 or Msk-1 activation as defined above, or a functionally conservative variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, or matrix/scaffold attachment. In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more inventive nucleic acid sequences, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art.

An "enhancer region" as used herein, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-a-vis the gene to be expressed, and may be enhancing, augmenting, improving, or ameliorating expression of more than one promoter. Promoter/enhancer sequences as defined above for the inventive expression vector, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter, neuron specific enolase promoter, calcium calmoduline kinase II, DARPP32 promoter, Nestine promoter, vGlut1 promoter, GAD promoter, serotonine (1-5)-receptor promoter). Alternatively, or in addition, they may include animal transcriptional control regions.

Additionally, the expression vector may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD). Exemplary expression vectors or their derivatives suitable for the invention particularly include, e.g. human or animal viruses (e.g. retrovirus, adenovirus, adeno-associated virus, herpes virus, vaccinia virus, poxvirus, poliovirus; lentivirus); insect viruses (e.g. baculovirus); yeast vectors; bacteriophage vectors (e.g. lambda phage); plasmid vectors such as pcDNA3 and cosmid vectors. Preferred expression vectors suitable for the invention are adenoviral vector such as helper-dependent adenoviral vectors and lentiviral vectors.

Another object of the invention is a pharmaceutical composition comprising at least one selective inhibitor of Elk-1 or MSK-1 activation for the prevention and/or treatment of mood and anxiety disorders.

Another object of the invention is a pharmaceutical composition comprising at least one selective inhibitor of Elk-1 or MSK-1 activation for use in the prevention and/or treatment of mood and anxiety disorders.

Another object of the invention is the use of at least one selective inhibitor of Elk-1 or Msk-1 activation for the preparation of a pharmaceutical composition for preventing and/or treating mood and anxiety disorders.

In one embodiment of the invention, said pharmaceutical composition comprises:
a) at least one selective peptide inhibitor as described here above;
b) a nucleic acid encoding said peptide as described here above; or
c) an expression vector comprising said nucleic acid as described here above.

In one embodiment of the invention, mood disorders comprise major depression disorder (i.e., unipolar disorder), mania, dysphoria, bipolar disorder, dysthymia, and cyclothymia.

In one embodiment of the invention, anxiety disorders comprise panic disorder, obsessive-compulsive disorder, post-traumatic stress disorder, social phobia, social anxiety disorder, specific phobias, generalized anxiety disorder In another embodiment of the invention, the peptide inhibitor of the invention or the pharmaceutical composition of the invention is for preventing and/or treating depression. Major depression is characterized by clinically significant depressions of mood and impairment of functioning as its primary clinical manifestations. Its clinical manifestations and current treatment overlap the anxiety disorders including panic-agorophobia syndrome, sever phobias, generalized anxiety disorder, social anxiety disorder, post-traumatic stress disorders and obsessive-compulsive disorder. Extremes of mood may be associated with psychosis, manifested as disordered or delusional thinking and perceptions, often congruent with the predominant mood. Depression often accompanies anxiety disorders and, when it does, it needs to be treated as well. Symptoms of depression include feelings of sadness, hopelessness, changes in appetite or seep, low energy, and difficulty concentrating. Most people with depression can be effectively treated with antidepressant medications, certain types of psychotherapy, or a combination of both.

Depressive disorders are expressed in different forms: Major depression is manifested by a combination of symptoms that interfere with the ability to work, study, sleep, eat, and enjoy once pleasurable activities. Such a disabling episode of depression may occur only once but more commonly occurs several times in a lifetime.

A less severe type of depression, dysthymia, involves long-term, chronic symptoms that do not disable, but keep one from functioning well or from feeling good. Many people with dysthymia also experience major depressive episodes at some time in their lives.

Another type of mood disorder is bipolar disorder, also called manic-depressive illness. Not nearly as prevalent as other forms of depressive disorders, bipolar disorder is characterized by cycling mood changes: severe highs (mania) and lows (depression). Sometimes the mood switches are dramatic and rapid, but most open they are gradual. When in the depressed cycle, an individual can have any or all of the symptoms of a depressive disorder. When in the manic cycle, the individual may be overactive, overtalkative; and have a great deal of energy. Mania often affects thinking, judgment, and social behavior in ways that cause serious problems and embarrassment. For example, the individual in a manic phase may feel elated, full of grand schemes that might range from unwise business decisions to romantic sprees. Mania, left untreated, may worsen to a psychotic state.

The peptide inhibitors of Elk-1 and MSK-1 activation of the invention, nucleic acid sequences encoding thereof or expression vectors comprising said nucleic acid sequences can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners.

In a therapeutic application, the selective peptide inhibitors of the invention are embodied in pharmaceutical compositions intended for administration by any effective means, including parenteral, topical, oral, pulmonary (e.g. by inhalation) or local administration. Preferably, the pharmaceutical compositions are administered parenterally, e.g., intravenously, subcutaneously, intradermally, or intramuscularly, or intranasally.

In one embodiment of the invention, the pharmaceutical composition of the invention is administered by intranasal route.

In another embodiment of the invention, the pharmaceutical composition of the invention is administrated intravenously.

In one embodiment, peptides that have the ability to cross the blood brain can be administered, e.g., systemically, nasally, etc., using methods known to those of skill in the art. In another embodiment, larger peptides that do not have the ability to cross the blood brain barrier can be administered to the mammalian brain via intracerebroventricular (ICV) injection or via a cannula using techniques well known to those of skill in the art.

In one embodiment, the invention provides compositions for parenteral administration that comprise a solution of peptide inhibitors of the invention, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for, example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the NAP or ADNF polypeptides are preferably supplied in finely divided from along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., J Mol Neurosci. 19(1-2):167-70 (2002)).

Another object of the invention is a method for treating anxiety and mood disorders in a subject in need thereof, said method comprising administering a therapeutically effective amount of at least one selective peptide inhibitor of Elk-1 or MSK-1 activation as described here above, or a therapeutically effective amount of a pharmaceutical composition as described here above.

In one embodiment, the peptide inhibitors of Elk-1 or MSK-1 activation of the invention are administered to a patient in an amount sufficient to prevent and/or treat anxiety and mood disorders. An amount adequate to accomplish this is defined as "therapeutically effective dose." Amounts effective for this use will depend on, for example, the particular peptide inhibitor employed, the type of disease or disorder to be prevented, the manner of administration, the weight and general state of health of the patient, and the judgement of the prescribing physician.

For example, an amount of peptide inhibitor falling within the range of a 100 ng to 10 mg dose given intranasally once a day (e.g., in the evening) would be a therapeutically effective amount. Alternatively, dosages may be outside of this range, or on a different schedule. For example, dosages may range from 0.0001 mg/kg to 10,000 mg/kg, and will preferably be about 0.001 mg/kg, 0.1 mg/kg, 1 mg/kg 5 mg/kg, 50 mg/kg or 500 mg/1 g per dose. Doses may be administered hourly, every 4, 6 or 12 hours, with meals, daily, every 2, 3, 4, 5, 6, for 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated.

In one embodiment of the invention, the selective inhibitors of Elk-1 and MSK1 are used in combination with classical antidepressant drugs including serotonin-selective reuptake inhibitors (SSRIs), such as fluoxetine (PROZAC®), norepinephrine reuptake inhibitors (NERIs), combined serotonin-norepinephrine reuptake inhibitors (SNRIs), monoamine oxidase inhibitors (MAOIs), phosphodiesterase-4 (PDE4) inhibitors or other atypical antidepressants, such as Tianeptine, Miltazapine.

In one embodiment of the invention, said method for treating anxiety and mood disorders in a subject in need thereof, further comprises the combined administration of at least one classical antidepressant drugs including, but not limited to, serotonin-selective reuptake inhibitors (SSRIs), norepinephrine reuptake inhibitors (NERIs), combined serotonin-norepinephrine reuptake inhibitors (SNRIs), monoamine oxidase inhibitors (MAOIs), phosphodiesterase-4 (PDE4) inhibitors or other atypical antidepressants.

The peptide was injected 90 min prior to the test; desipramine 30 min according to standard protocols (A). The scrambled control peptide (B) and the MEK inhibitor SL327 (C) are of no effect in this paradigm. The TAT-DEF-Elk-1 peptide does not affect horizontal locomotion (D). Data were analysed with a one-way ANOVA and Duncan's post-hoc (* indicates $p<0.05$).

Figure 3:
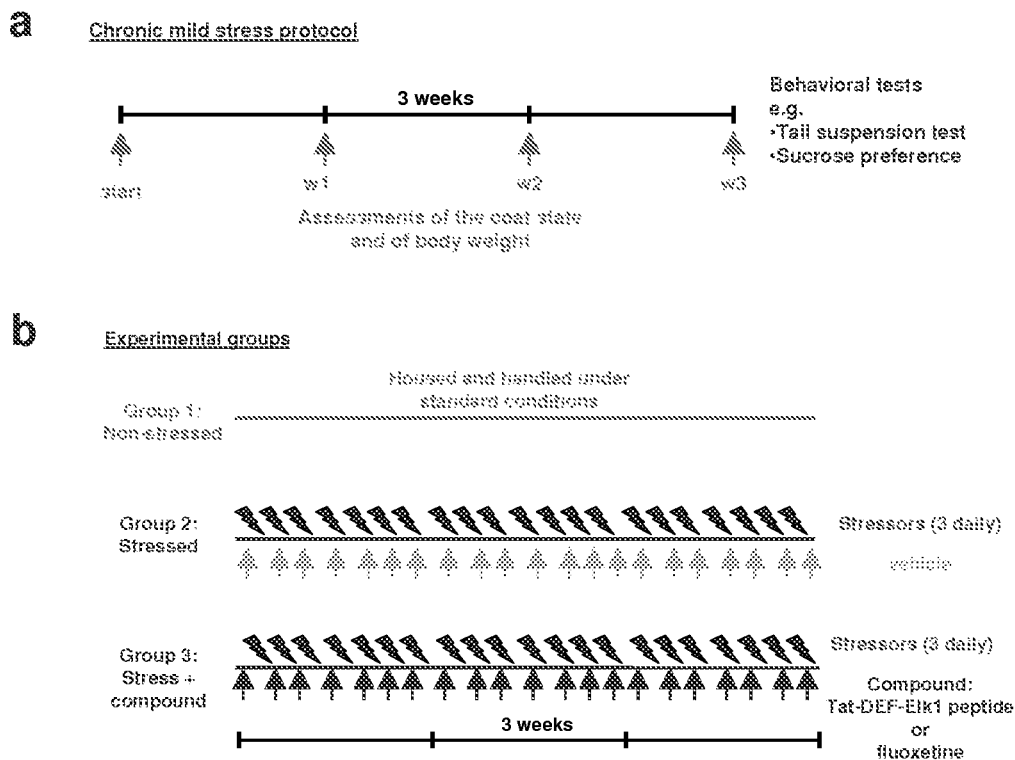

FIG. 3. Unpredictable chronic mild stress protocol and experimental groups.

Figure 4:
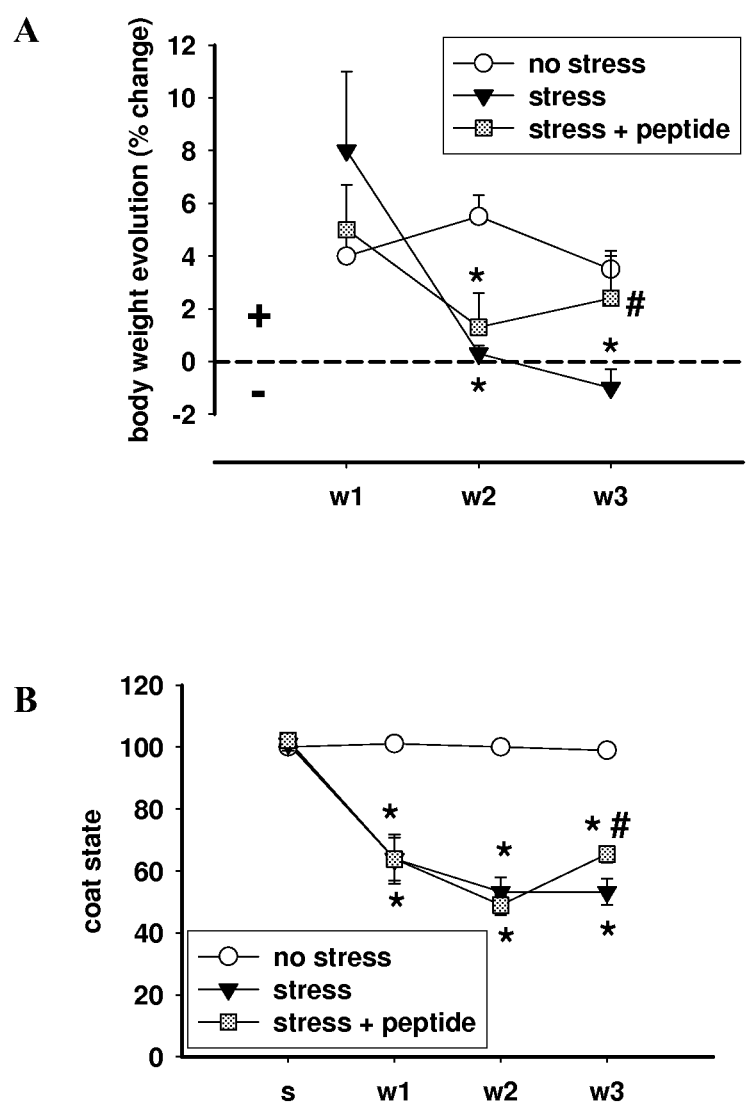

FIG. 4. In the UCMS paradigm, the TAT-DEF-Elk-1 peptide induces antidepressant-like effects.

(A) There is a progressive weight loss in stressed animals (black triangles) as compared to non-stressed animals (white circles). This loss is reversed by administration of the peptide during the UCMS (grey squares). (B) There is a progressive degradation of the coat state in stressed animals (black triangles) as compared to non-stressed animals (white circles). This degradation is reversed partially by administration of the peptide during the UCMS (grey squares). Data were analysed with repeated measures ANOVA and Duncan's post-hoc (* indicates $p<0.05$ as compared to non-stressed; # indicates $p<0.05$ as compared to stressed).

Figure 5:
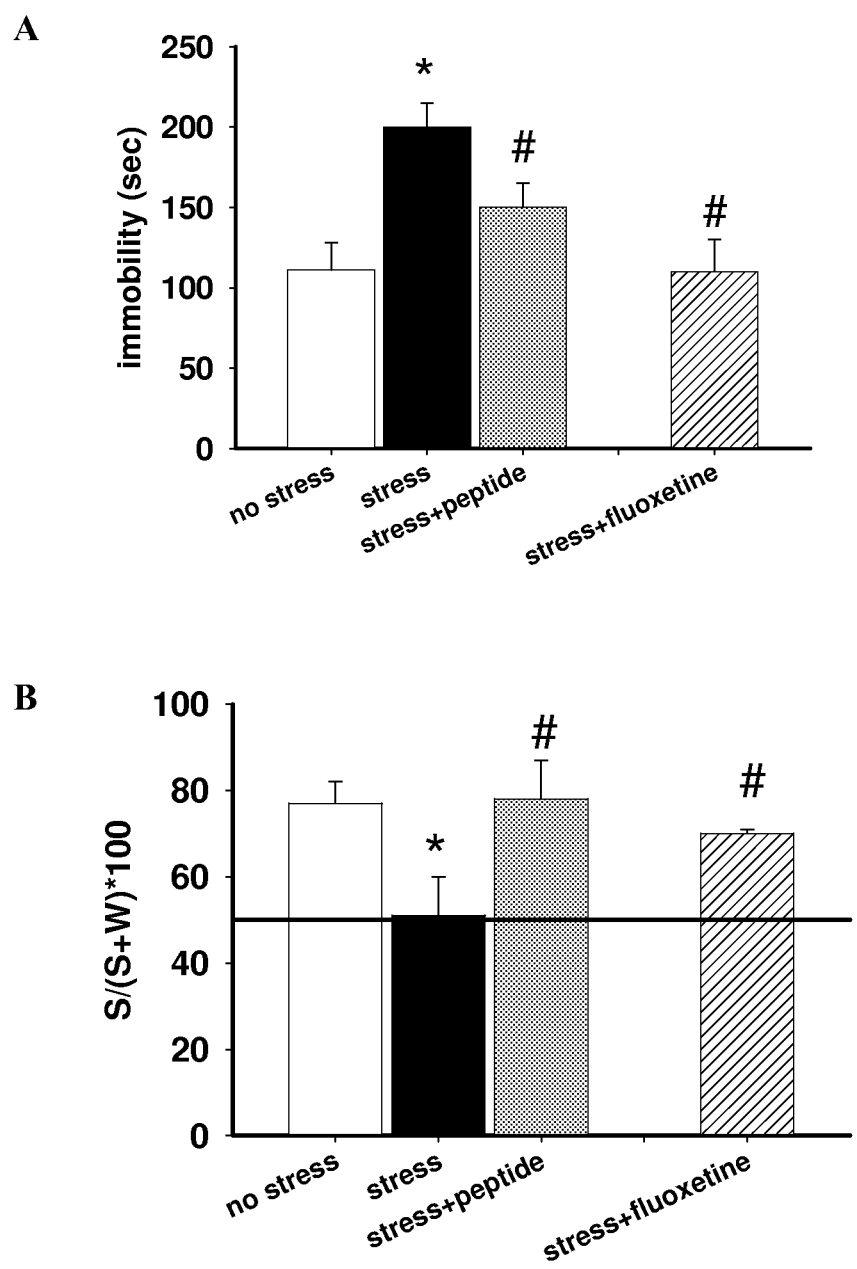

FIG. 5. In the UCMS paradigm the TAT-DEF-Elk-1 peptide induces antidepressant-like effects.

(A) There is an increase in immobility in the TST in stressed animals (black bar) as compared to non-stressed animals (white bar). This is reduced by administration of the peptide during the UCMS (grey bar). (B) There is a loss of sucrose preference (expressed as the % of sugar of the total consumption of the animal (sugar+water)) in stressed animals (black bar) as compared to non-stressed animals (white bar). This is reversed by administration of the peptide during the UCMS (grey bar). Data were analysed with one-way ANOVA and Duncan's post-hoc (* indicates $p<0.05$ as compared to non-stressed; # indicates $p<0.05$ as compared to stressed).

Figure 6:
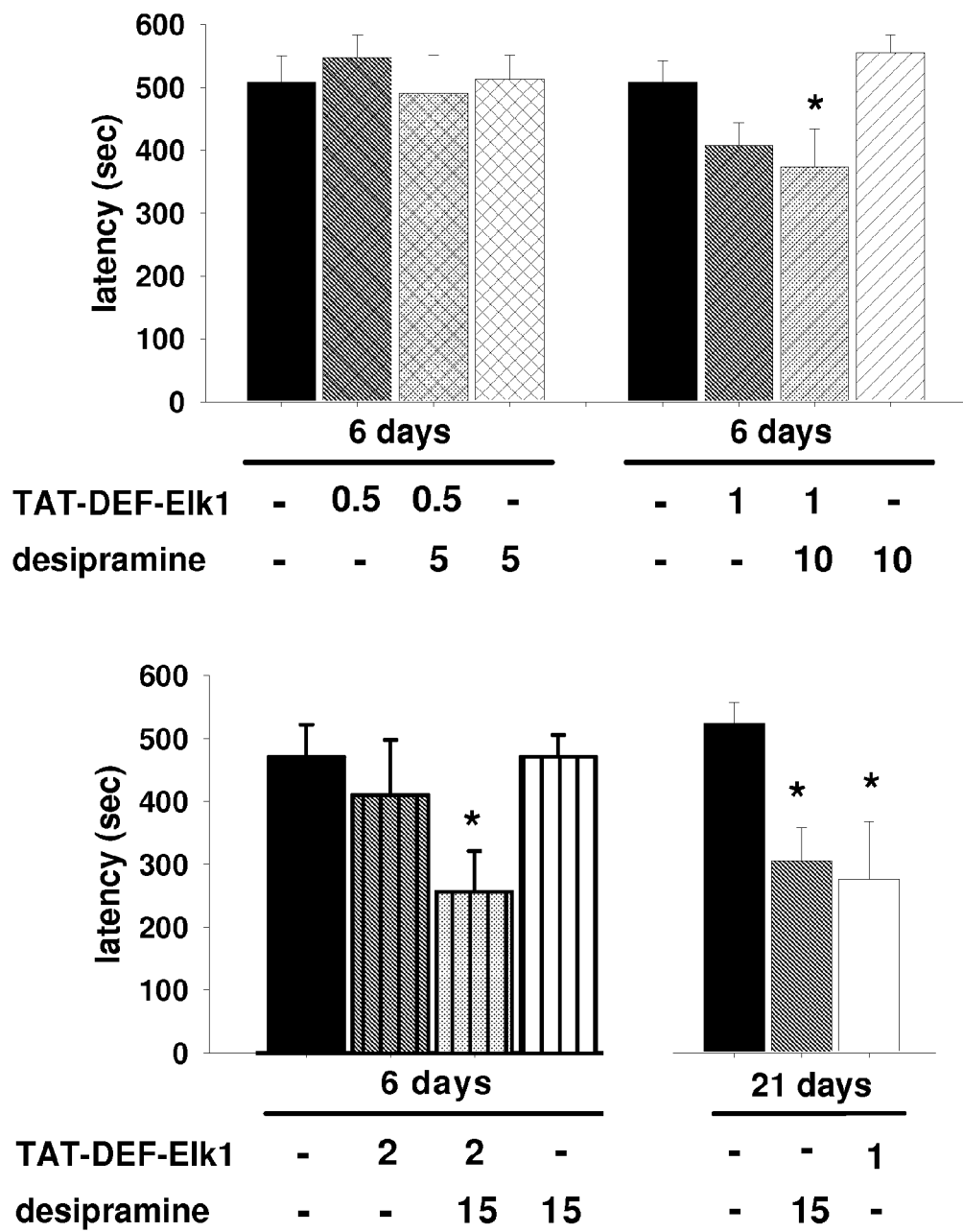

FIG. 6: Association of the TAT-DEF-Elk1 peptide with the reference antidepressant desipramine markedly and dose dependently reduces delay of onset of action in the novelty hypophagia test.

Data represent means+/-SE of latency to consume a palatable treat when this is presented to the animal in a stressful environment; *$p<0.05$ as compared to saline treated.

Figure 7:
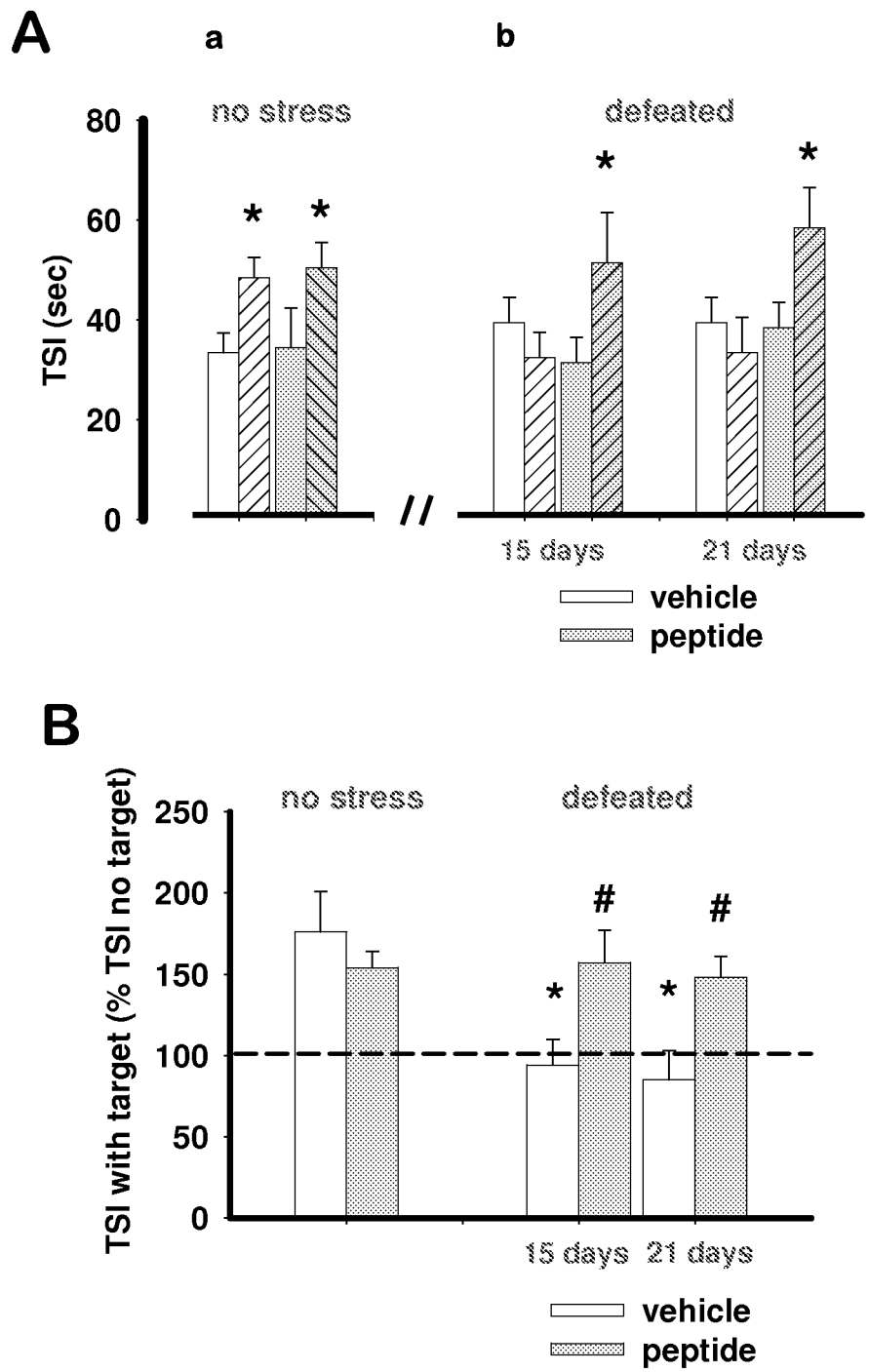

FIG. 7: The TAT-DEF-Elk1 peptide reduces social avoidance in the social defeat stress (SDS) test.

(A) Data represent means+/-SE of time spend interacting (TSI) with the cage, in the absence (non-hatched bars) or presence (hatched bars) of the target. When target is present, control mice engage in active social behaviour, seen as an increase of TSI (panel a), while vehicle-treated defeated mice (panel b; white bars) show lower TSI, indicating social avoidance. Treatment with TAT-DEF-Elk1 (grey bars) fully reverses this behaviour. *$p<0.05$ vs TSI in the absence of target.

(B) The same results were plotted as percentage values. *$p<0.01$ vs non-defeated, #$p<0.05$ vs defeated treated with vehicle.

Figure 8:
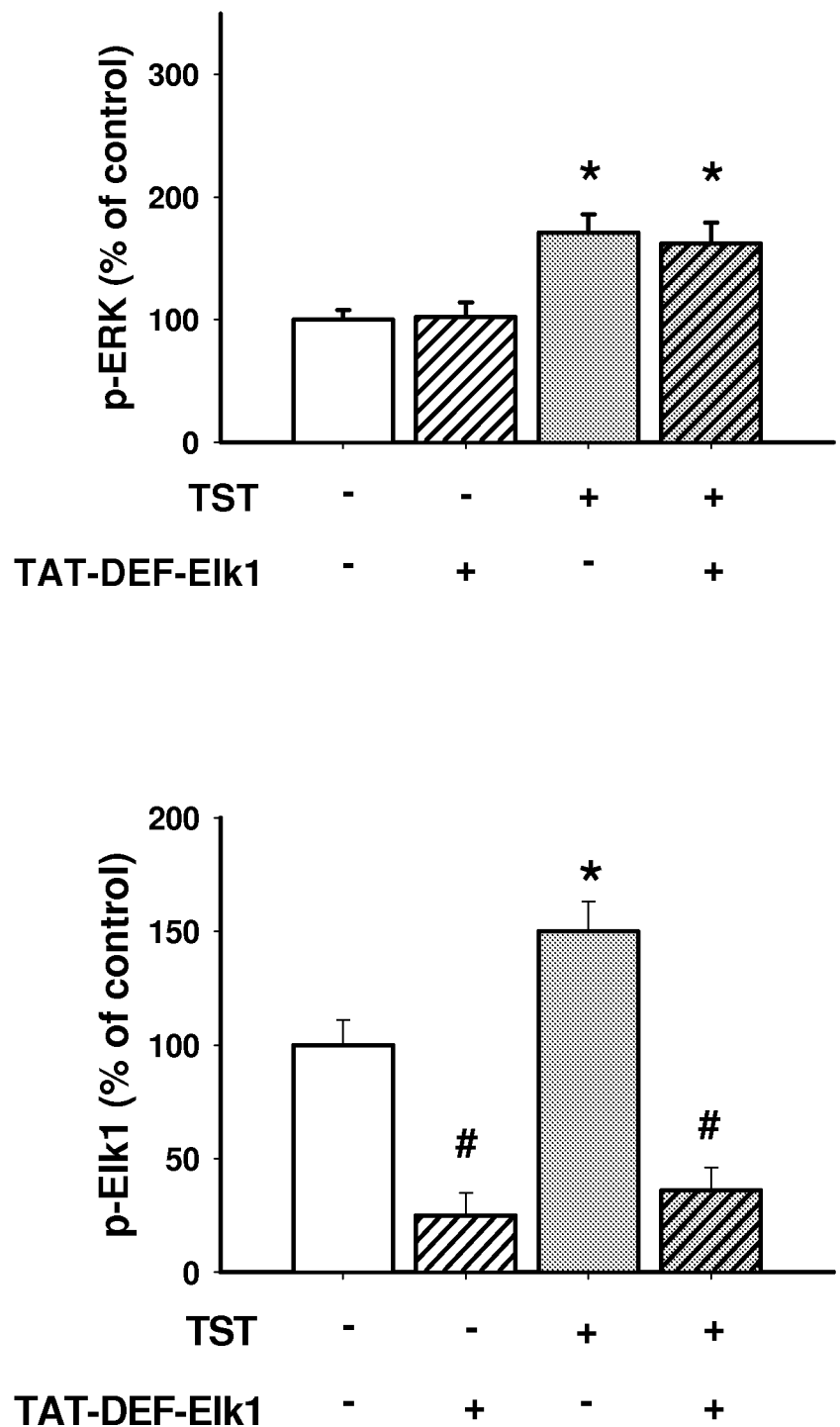

FIG. 8: The TAT-DEF-Elk-1 peptide reduces tail suspension-induced Elk1 phosphorylation in the medial prefrontal cortex (mPFCx).

*$p<0.05$ as compared to no-stressed mice receiving the same treatment

$p<0.05$ as compared to vehicle-treated no-stressed or stressed mice.

Figure 9:
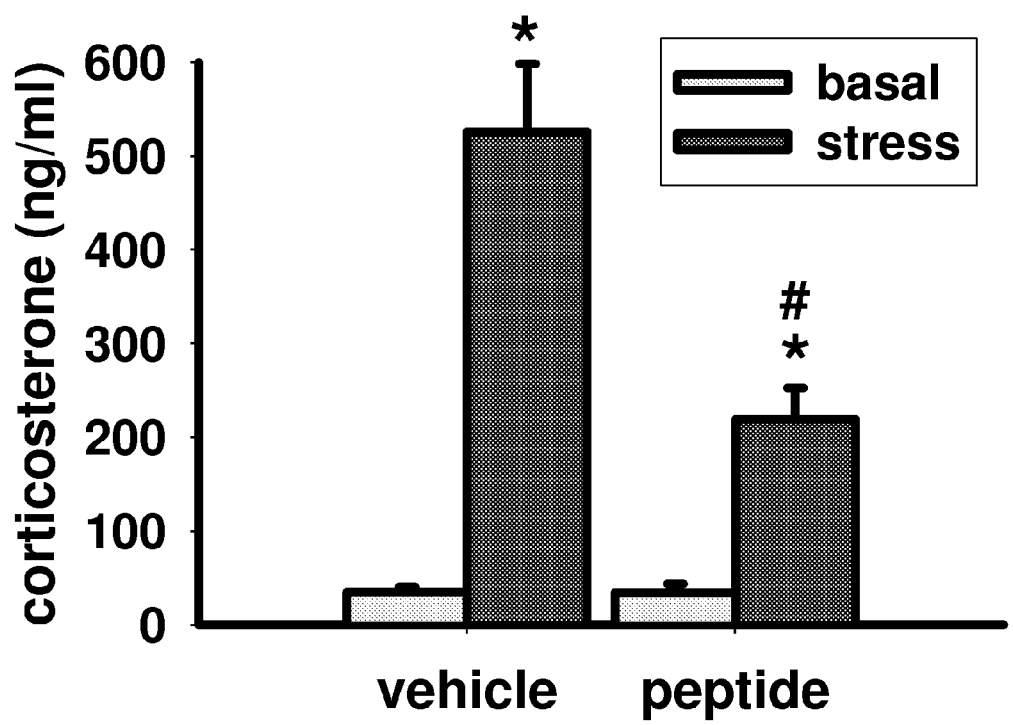

FIG. 9: The TAT-DEF-Elk1 peptide markedly reduces stress induced increase in plasma corticosterone.

Data represent means+/-SE of plasma corticosterone in banal conditions (non-stressed, light grey bars) and immediately after a 30-min restraint stress (dark grey bars); vehicle or the TAT-DEF-Elk1 peptide were administered 1 h before the beginning of stress; *$p<0.05$ as compared to non-stressed; #$p<0.05$ as compared to vehicle-treated.

EXAMPLES

TAT-DEF-Elk-1 peptide (GRKKRRQRRRPPSPAKLS-FQFPSSGSAQVHI (SEQ ID NO:28)) was tested in two different learned helplessness tests, the mouse tail suspension test (TST) and the mouse forced swimming test (FST).

In these tests experimental animals are exposed to inescapable aversive situations (hanging by the tail, being into the water) and in response show alternate periods of agitation and immobility reflecting "attempts to escape" and 'behavioural resignation" respectively. The FST and the TST are widely used to predict antidepressant activity; acute treatment with antidepressants increases active escape attempts, thus reducing immobility (e.g. Svenningsson et al., PNAS, 2002; Li et al., Neuropharmacol, 2001).

The details of the experimental protocols used are as follows: mice were injected i.p. with vehicle, different doses of the peptide TAT-DEF-Elk-1, of a scrambled peptide (serving as control), of the MEK inhibitor SL327, or with the reference antidepressants fluoxetine (20 mg/kg) or desipramine (20 mg/kg), at appropriate time points before the test trial.

In the TST, each mouse was tested in an individual cubicle while suspended from a tail hanger with adhesive tape wrapped around its tail (1.5-2 cm from tip) 80 cm above the floor. The trial was conducted for 5 min, during which the duration of immobility was measured automatically (BIO-SEB, France). For the FST, mice were placed in clear plastic cylinders (diameter 10 cm; height 25 cm) filled with water at 6 cm height (22-25° C.) for 6 min. A blinded observer scored the duration of immobility manually during the last 4 min of the 6-min test.

Figure 1:
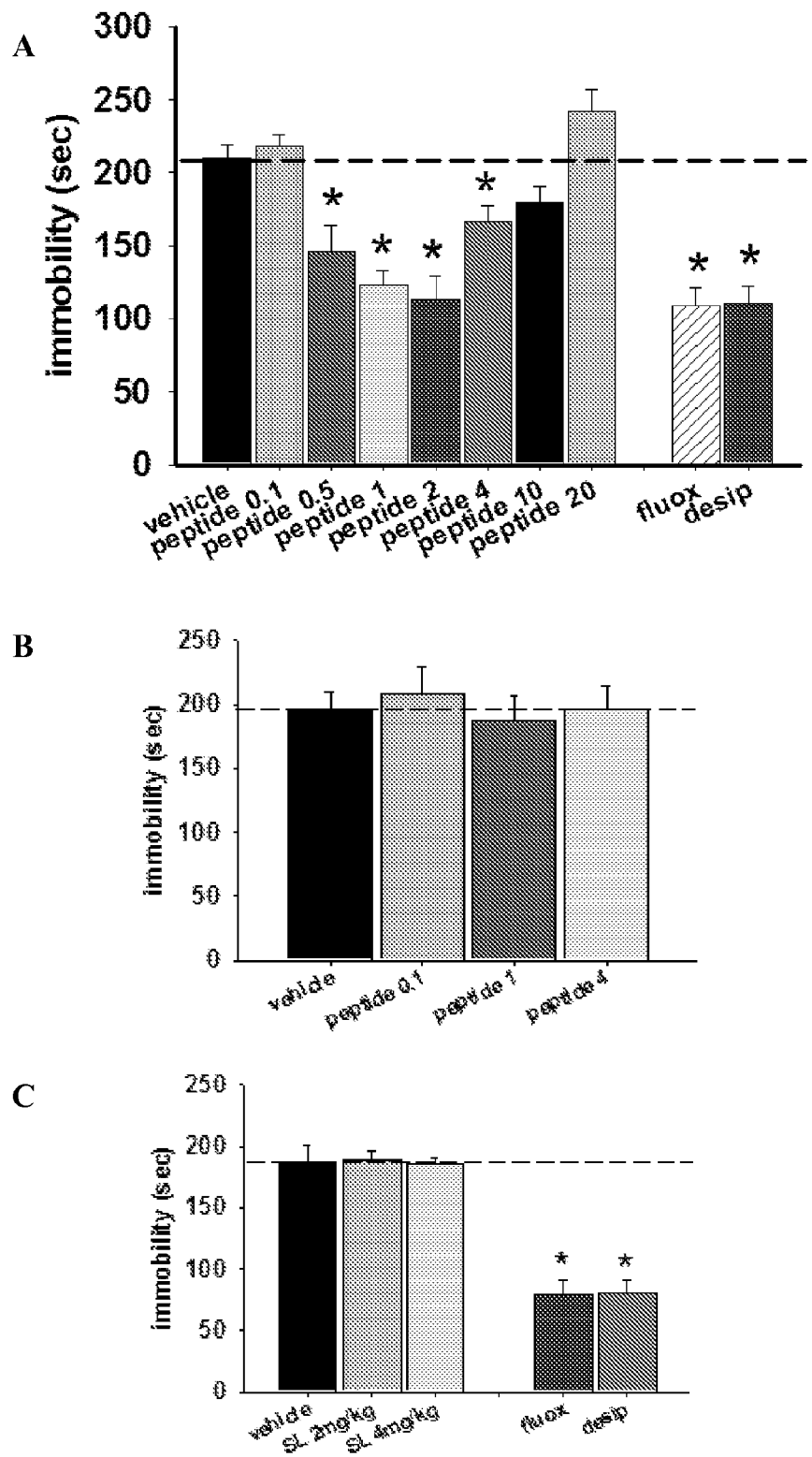
FIG. 1. In the TST, the TAT-DEF-Elk-1 peptide induces antidepressant-like effects similar to the classical antidepressants fluoxetine and desipramine (A). The peptide was injected 90 min prior to the test; desipramine and fluoxetine 30 min according to standard protocols. The scrambled control peptide (B) and the MEK inhibitor SL327 (C) are of no effect in this paradigm. Data were analysed with a one-way ANOVA and Duncan's post-hoc (* indicates $p<0.05$).

As shown in FIG. 1, the TAT-DEF-Elk-1 peptide reduced immobility in the TST similar to classical antidepressants; the maximum effect of the TAT-DEF-Elk-1 peptide was of similar magnitude of that of fluoxetine and desipramine. The U-inverted shape curve of the effects of the TAT-DEF-Elk-1 peptide might be related to non-specific effects seen with high doses of the peptide.

Figure 2:
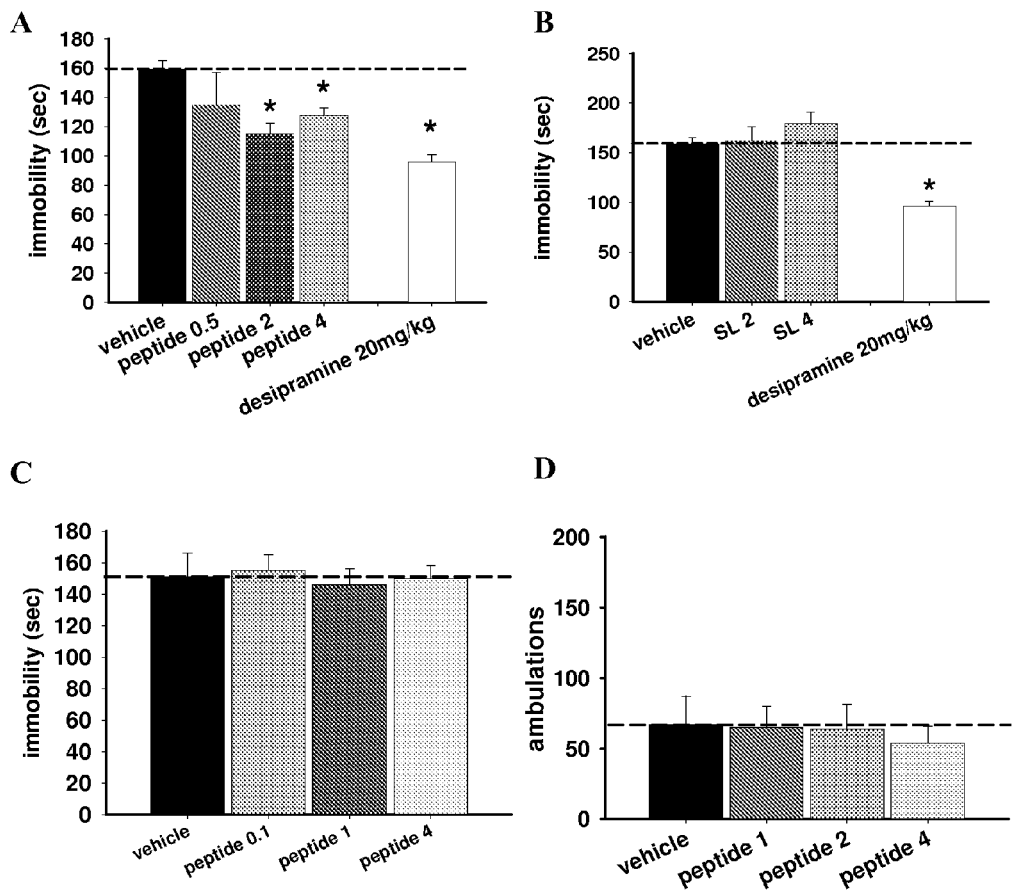
FIG. 2. In the FST, the TAT-DEF-Elk-1 peptide induces antidepressant-like effects similar to the classical antidepressant desipramine.

Furthermore, the TAT-DEF-Elk1 peptide also induced antidepressant-like effects in the FST at the same doses that were effective in the TST (FIG. 2A). On the other hand, the scrambled control peptide and the SL327 had no effect in the FST (FIG. 2B, 2C).

The increases in immobility seen in the TST and FST reflect antidepressant action of the TAT-DEF-Elk1 peptide since at these doses it did not affect locomotor activity (FIG. 2D).

We have also assessed the effects of the TAT-DEF-Elk1 peptide in the unpredictable chronic mild stress paradigm (UCMS). UCMS is used as a pertinent model of depression with aetiological validity. In UCMS protocols animals are subjected for a long period to different non-anticipated stressors. Chronic exposure to stress results to a syndrome in mice that reproduces symptoms of depression, including increased resignation, anxiety-like behavior, decreased consumption of palatable food, and physiological changes. Chronic administration of compounds with antidepressant activity reverses these changes.

The protocol that we have used consists of three weeks of UCMS, during which mice were subjected to various stressors according to a 'random' schedule. Body weight and coat state were assessed weekly, as markers of the progression of the UCMS-evoked syndrome. At the end of the 3 week period the emotional state of the mice was tested in behavioral tests of emotionality and of depression-like behaviors (FIG. 3A).

Experimental groups of mice were as follows:
(i) non-stressed mice: these were group housed and were handled and maintained under standard laboratory conditions (Group 1; FIG. 3B),
(ii) stressed mice: these were maintained under standard laboratory conditions but were isolated in small individual cages. During the three week protocol they were exposed to three mild stressors per day. Stressed-mice were treated either with vehicle (Group 2; FIG. 3B), with the peptide (1 mg/kg; once daily), or with the reference antidepressant fluoxetine (20 mg/kg; once daily) (Group 3; FIG. 3B). Treatment with vehicle or compounds started at the beginning of the UCMS and lasted throughout the three week period.

As shown in FIG. 4 the TAT-DEF-Elk1 peptide has an antidepressant-like profile in the UCMS paradigm.

Namely, treatment with the TAT-DEF-Elk1 peptide reversed the progressive weight loss induced by UCMS (FIG. 4A). A full reversion of body weight loss was visible at the end of the third week post-stress, indicating that a prolonged administration of the TAT-DEF-Elk1 peptide was necessary to induce this effect, as is the case with classical antidepressants. The TAT-DEF-Elk1 peptide also diminished the degradation of the coat state that is induced by UCMS (FIG. 4B). The partial reversal of coat degradation was also seen only after two weeks of administration of the TAT-DEF-Elk1 peptide, as is the case with classical antidepressants.

At the end of the UCMS paradigm, mice were tested for depressive-like responses, such as passivity and resignation measured as increased immobility in the tail suspension test and anhedonia measured as the preference to sucrose.

The TAT-DEF-Elk1 peptide reduced UPMS-induced immobility in the TST (FIG. 5A) and fully restored UCMS-blunted sucrose preference (FIG. 5B), similarly to the reference antidepressant fluoxetine.

Antidepressant action of TAT-DEF-Elk1 peptide was confirmed using two additional models: (i) the novelty hypophagia test and (ii) the social defeat test.

In the novelty hypophagia test, TAT-DEF-Elk1 peptide (0.5, 1 and 2 mg/kg), desipramine (5, 10 and 15 mg/kg), a combination of the two or vehicle were administered 6 or 21 days before the test as indicated in FIG. 6. Results show that association of the TAT-DEF-Elk1 peptide with the reference antidepressant desipramine markedly and dose dependently reduces delay of onset of action in the novelty hypophagia test. After chronic administration (21 days), the effect of TAT-DEF-Elk1 peptide is similar to the effect of desipramine. However, delay of onset of action in the test is observed only after subchronic treatment (6 days) with administration of a combination of TAT-DEF-Elk1 peptide and desipramine.

In the social defeat stress test (SDS), mice were exposed repeatedly (2 week) to aggressive mice; controls were gently handled. Subsequently, the aggressors were removed. Mice were treated with vehicle or TAT-DEF-Elk1 (1 mg/kg) for 15 or 21 days, and then tested for SDS-induced social avoidance. The test box contained a perforated plastic cage that was empty for the first test session and that held a neutral mouse (target) for the second test session.

Results show that desipramine did not have any effect on SDS-induced social avoidance after either 15 or 21 days of treatment (data not shown). FIG. 7 shows that the TAT-DEF-Elk1 peptide is active after only 15 days of administration which is consistent with a reduced delay of onset of action. For comparison, it has been described in the literature that imipramine has an antidepressant action in the SDS test only after 39 days of administration.

Results presented in FIG. 8 and FIG. 9 provide in vivo biochemical evidence on efficacy and specificity of action of TAT-DEF-Elk1 peptide in targeting molecular substrates relevant to mood disorders.

In the first experiment, TAT-DEF-Elk-1 peptide (2 mg/kg) or vehicle were administrated 1 h30 before a 10 min tail suspension trial (TST). Mice were perfused 20 min after starting the TST test and phosphorylation of ERK and Elk1 was assessed with immunochemistry. Results shown in FIG. 8 demonstrate that TAT-DEF-Elk1 peptide reduces selectively tail suspension-induced Elk1 phosphorylation in the medial prefrontal cortex (mPFCx) as it does not inhibit tail suspension-induced ERK phosphorylation.

In the second experiment C57BL/6J mice (10 weeks old) were injected with TAT-DEF-Elk1 peptide or vehicle; 1 h30 after the injection the mice were subjected to a 30 min restraint stress i.e. mice were confined individually in a 50 ml Falcon tube in which a hole was made at the top for the mice to breathe. Mice were decapitated directly after restraint, blood was collected in 2 ml eppendorfs containing EDTA at 4° C. Samples were centrifuged for 15 min at 760 g, plasma was collected and corticosterone assessed using the Corticosterone Double Antibody 125-I RIA kit (MP BIOMEDICAL).

Results shown in FIG. 9 demonstrate that TAT-DEF-Elk1 peptide markedly reduces stress induced-elevations in plasma level corticosterone but does not affect basal plasma level corticosterone.

REFERENCES

Svenningsson P et al. (2002) Involvement of striatal and extrastriatal DARPP-32 in biochemical and behavioral effects of fluoxetine (Prozac). Proc Natl Acad Sci USA 99:3182-87.

Li X et al. (2001) Antidepressant-like actions of an AMPA receptor potentiator (LY392098). Neuropharmacology 40:1028-33.

Manji H K et al. (2003) Enhancing neuronal plasticity and cellular resilience to develop novel, improved therapeutics for difficult-to-treat depression. Biol Psychiatry 53:707-42. Review

The invention claimed is:

1. A method for treating or preventing depression in a subject in need thereof, said method comprising administering a therapeutically effective amount of at least one selective peptide inhibitor of E twenty-six (ETS)-like transcription factor 1 (Elk-1) activation or a therapeutically effective amount of a pharmaceutical composition comprising such a selective peptide inhibitor of Elk-1 activation,
wherein said peptide inhibitor is a peptide comprising at least one cell penetrating sequence and at least one docking domain sequence where the docking domain is a peptide consisting of the amino acid sequence SPAKLSFQFPSSGSAQVHI (SEQ ID NO:1).

2. The method according to claim 1, further comprising the combined administration of at least one antidepressant drug.

3. The method of claim 1, wherein said cell penetrating sequence is chosen from the group consisting of HIV-TAT sequence (SEQ ID NO: 4); Penetratin (SEQ ID NO: 5); and amino acid sequences of SEQ ID NO: 6 to 10 and of (SEQ ID NO: 15 to 19.

4. The method of claim 1, wherein said peptide inhibitor has the sequence of SEQ ID NO: 28.

* * * * *